(12) United States Patent
Mott et al.

(10) Patent No.: US 7,533,557 B1
(45) Date of Patent: May 19, 2009

(54) IMPACT TENSILE TEST MACHINE

(75) Inventors: Peter H Mott, Washington, DC (US);
Charles M Roland, Waldorf, MD (US);
Howard L Schrader, White Plains, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 47 days.

(21) Appl. No.: 11/959,216

(22) Filed: Dec. 18, 2007

(51) Int. Cl.
*G01M 7/00* (2006.01)
(52) U.S. Cl. ........................... 73/12.14; 73/760
(58) Field of Classification Search ............. 73/12.14, 73/760
See application file for complete search history.

(56) References Cited

U.S. PATENT DOCUMENTS

| | | | |
|---|---|---|---|
| 3,885,424 A * | 5/1975 | Ryckman et al. | 73/860 |
| 4,501,139 A * | 2/1985 | Petersen | 73/117.01 |
| 4,535,636 A * | 8/1985 | Blackburn et al. | 73/831 |
| 4,930,355 A | 6/1990 | Heck | |
| 5,251,491 A * | 10/1993 | Nakaoka et al. | 73/862.41 |
| 5,431,060 A * | 7/1995 | Lauren | 73/831 |
| 7,320,242 B2 * | 1/2008 | Hoo Fatt et al. | 73/12.14 |
| 2004/0040369 A1 | 3/2004 | Hoo Fatt et al. | |

OTHER PUBLICATIONS

C. M. Roland, Rubber Chem. Technol. 79, 429 2006.
B. Hopkinson, Philos. Trans. R. Soc. London, Ser. A 213, 437 1914.
H. Kolsky, Proc. Phys. Soc. London, Sect. B 62, 676 1949.
G. J. Albertoni, Rubber Chem. Technol. 10, 317 1937.
F. L. Roth and W. L. Holt, Rubber Chem. Technol. 13, 348 1940.
D. S. Villars, J. Appl. Phys. 21, 565 1950.
A. Gale and N. J. Mills, Plast. Rubber Process. Applic. 5, 101 1985.
K. G. Hoge and R. J. Wasley, J. Appl. Polym. Sci.: Appl. Polym. Symp.12, 97 1969.
J. A. Rinde and K. G. Hoge, J. Appl. Polym. Sci. 15, 1377 1971.
J. Yi, M. C. Boyce, G. F. Lee, and E. Balizer, Polymer 47, 319 2006.
L. M. Yang and V. P. W. Shim, Int. J. Impact Eng. 31, 129 2005.

(Continued)

*Primary Examiner*—Max Noori
(74) *Attorney, Agent, or Firm*—John J Karasek; Amy Ressing

(57) ABSTRACT

A high-speed tensile test device is disclosed, which measures the stress-strain behavior, up to failure, of polymeric materials, at high strains (as much as 1000%), and high strain rates (up to $10^4$/s). A weight, when dropped down a vertical track, impacts two L-levers positioned below and on each side of the weight, pushing the horizontal arms of the L-levers. The L-levers have cable connected to the vertical arms of the L-levers and are looped around pulleys, then connected to shuttles located on a horizontal track. The shuttles are attached to load cells, which are connected to grips that hold a sample to be tested. When the horizontal arms of the L-levers are pushed by the weight, they pivot, causing the cables to pull on the shuttles, load cell, and grip, which move in an outward direction, stretching the sample.

8 Claims, 16 Drawing Sheets

OTHER PUBLICATIONS

B. Song and W. Chen, J. Eng. Mater. Technol. 125, 294 2003.
P. J. Rae and E. N. Brown, Polymer 46, 8128 2005.
W. Chen, B. Zhang, and M. J. Forrestal, Exp. Mech. 39, 81 1999.
P. H. Mott and C. M. Roland, Rubber Chem. Technol. 68, 739 1995.
M. L. Anderson, P. H. Mott, and C. M. Roland, Rubber Chem. Technol. 77, 293 2004.
I. Bekar, M. S. Hoo Fatt, and J. Padovan, Tire Sci. Technol. 30, 45 2002.
M. S. Hoo Fatt and I. Bekar, J. Mater. Sci. 39, 6885 2004.
I. S. Choi, C. M. Roland, and L. C. Bissonnette, Rubber Chem. Technol. 67, 892 1994.
A. N. Gent and P. Marteny, J. Appl. Phys. 53, 6069 1982.
Roland, et. al., High Strain Rate Mechanical Behavior of polyurea, Polymer 48 (2007) 574-578.
J. K. Knowles, J. Appl. Math. 62, 1153 2002.
Yeh, et al., Transient Simulation of Solder Joint Fracturing Under Impact Test, 2004 Electronics Packaging Technology Conference.
Mott, et al., High-speed tensile test instrument, Review of Scientific Instruments 78, 045105 2007.

\* cited by examiner

IMPACT TENSILE TEST MACHINE

BACKGROUND OF THE INVENTION

The use of elastomers for high strain rate applications, such as skid resistant tire treads, mechanical capacitors, and coatings for impact resistance and acoustic damping, requires the ability to measure the stress-strain behavior to failure at high strain rates, for example, greater than 10 s$^{-1}$. Often the function of such materials in high strain rate applications is to absorb energy. The amount of absorbed energy is related to the area under the stress-strain curve. The stress-strain behavior of polymers depends strongly on the strain rate; that is, elastomers are highly viscoelastic. The strain rate in many applications is higher than that measured with conventional experimental tests. Characterizing elastomers at high strain rates is difficult, even at small amplitudes.

Typical dynamic mechanical spectrometers are limited to frequencies below about 100 Hz, although custom-built instruments have attained 10 kHz. Atomic force microscopes ("nanoindenters") operate as high as 1 MHz but only probe the surface. While time-temperature superpositioning is often invoked to extend the effective frequency range of test data, the results are inaccurate for measurements in the glass transition zone. Unfortunately, this is often the regime of interest if very high frequency results are required. The difficulties of high strain rate testing are exacerbated if the behavior at high strains is to be measured. Even though unfilled rubber can be linearly viscoelastic to fairly large strains (about 100%), it is generally not possible to apply Boltzmann superpositioning to deduce the properties at high strains from low strain experiments.

There are available high speed tensile test machines. However, most do not provide the full stress-strain to failure curves to high elongation. While present-day devices, such as the tensile split Hopkinson pressure bar and the expansion ring tests, can provide dynamic stress-strain curves at very high rates, they are not designed to monitor how the specimen fractures. Moreover, there is a mixed mode of deformation, which does not correspond to homogeneous strain such as uniaxial deformation. There is a need for a tensile impact test machine that gives both dynamic stiffness and strength characteristics of rubber and soft polymeric materials and is capable of monitoring specimen fracture.

The stress-strain response of polymeric materials to high strains (up to about 10) at high strain rates (up to about 10$^4$ s$^{-1}$) is an unexplored area of behavior. The performance in such applications often depends on the details of the stress-strain response, which for polymers depends strongly on strain rate. A number of devices have been developed for measuring the mechanical response of polymers at high speed, but many do not allow visual observation of specimen deformation and failure. Other devices, such as the split Hopkinson pressure bar, are limited in the range of strain that can be applied. See B. Hopkinson, Philos. Trans. R. Soc. London, Ser. A 213, 437 (1914) and H. Kolsky, Proc. Phys. Soc. London, Sect. B 62, 676 (1949).

Previously, various methods have been explored for measurement of the mechanical response of elastomers at high strain rates. Albertoni, et al, Rubber Chem. Technol. 10, 317 (1937) modified a pendulum hammer to stretch a ring-shaped test piece to a predetermined elongation at constant strain rates up to about 40 s$^{-1}$. A pin is placed at a predetermined distance, which disengages the test specimen from the pendulum. Following the release of the rubber sample, the pendulum continues to a new height, as determined by the retained energy. The difference in the initial and follow-through heights of the pendulum yields the energy to deform the sample. A different test specimen is used for each point, so that by repeated tests at various strains (i.e., pin positions) the stress/extension curve is obtained. Note however that the stress at any given strain corresponds to the average of all lower strains; this means that the secant modulus value is measured, not the actual tangent modulus.

Roth and Holt, Rubber Chem. Technol. 13, 348 (1940), designed an instrument that used a falling weight, achieving strain rates up to 20 s$^{-1}$. A ring-shaped specimen is stretched by the falling weight, whose position is recorded on paper tape during the course of its descent. From the position versus time information, the work done on the sample is calculated. From this work input, in combination with the displacement data, the stress is obtained as a function of strain. The strain rate varies during the experiment. Different masses of the falling weight are used to map out the stress-strain curve. Note that the strain rate is not constant and the obtained modulus for any strain is the secant modulus (the average response of the sample over all strains up to the given strain), not the actual tangent modulus.

Villars, J. Appl. Phys. 21, 565 (1950), achieved strain rates as high as 2700 s$^{-1}$ with a device employing a spinning wheel. A pin on the edge of the wheel grabs a rubber sample in the form of a loop, stretching it at an approximately constant rate. The speed of the spinning wheel is varied between 60 and 1700 rpm by a transmission and with speed-reducing pulleys. A piezoelectric crystal and oscilloscope is used to measure the force.

Gale and Mills, Plast. Rubber Process. Applic. 5, 101 (1985), achieved compressive strain rates approaching 200 s$^{-1}$ with a falling weight apparatus. The 5 kg weight is dropped onto the sample, compressing it. Integration of accelerometers attached to the weight gives the energy required for compression of the rubber. The slowing of the falling weight is used to deduce the rebound (recovery) of the compressed sample. Thus, a measure of the energy input to and dissipated by the sample is obtained. Approximate force and displacement curves for foam test samples were obtained. The rate is not constant, the mode of deformation in not homogeneous, and the stress-strain data is only semi-quantitative.

Hoge and Wasley, J. Appl. Polym. Sci.: Appl. Polym. Symp. 12, 97 (1969), and Rinde and Hoge, J. Appl. Polym. Sci. 15, 1377 (1971), obtained high speed stress/strain measurements on a polystyrene foam by using the gas gun from a metal working machine (Dynapak Model 600). Release of the compressed gas expands a piston, which in turn compresses a foam sample at rates up to 100 s$^{-1}$. A plate behind the sample limits the strain of the sample to 5% in compression. The force and displacement of the sample are measured with transducers. According to the authors the test method "does not provide valid modulus data", particularly at low strains.

The instrument most commonly used to measure high speed mechanical behavior is the split Hopkinson bar, originally developed for steel but since applied to other materials, including polymers. See Yi et al., Polymer 47, 319 (2006). In the split Hopkinson bar device, a sample is placed between two long elastic bars, typically aluminum. A third, smaller "striker" bar is accelerated toward the incident bar. The reflected and transmitted pulses are measured, usually with strain gauges attached to the bars, and from these the properties of the sample are deduced. The requirement of dynamic stress uniformity limits the maximum deflection and minimum strain rate. See, Yang et al, Int. J. Impact Eng. 31, 129 (2005), Song et al., J. Eng. Mater. Technol. 125, 294 (2003), Rae et al., Polymer 46, 8128 (2005), Yi et al., Polymer 47, 319

(2006), Sarva et al, Polymer 48, 2208 (2007), and Amirkhizi et al., Philos Mag, 86, 5847 (2006)

The recent development of pulse shaping in the Hopkinson bar method provides nearly constant strain rates to moderate strains. See, Chen et al., Exp. Mech. 39, 81 (1999). For elastomers, spatially homogeneous uniaxial compression is difficult to achieve due to the tendency of these materials to adhere to the loading surface. This adhesion causes subtle "bulging," indicative of mixed modes of deformation, for example, compression in the central region and shear at the interfaces. For thin cylinders this "barreling" necessitates a large correction of the measured data. See Gent et al., Proc. Inst. Mech. Eng. 173, 111, 1959; Mott et al., Rubber Chem. Technol. 68, 739 (1995); and Anderson, et al., Rubber Chem. Technol. 77, 293 (2004). Verification of truly flat cylindrical surfaces is complicated by the tradeoff between time and spatial resolution in the imaging of high speed measurements. See Song et al., J. Eng. Mater. Technol. 125, 294 (2003).

Hoo Fatt et al describe another high speed tensile test machine in Tire Sci. Technol. 30, 45 (2002); U.S. Patent application No. 20040040369; and Hoo Fatt et al., J. Mater. Sci. 39, 6885 (2004). In that device, the impact energy is supplied by a Charpy-type pendulum, which contacts a slider bar that pulls directly on cables attached to shuttles; sample grips are attached to the latter. FIG. 1 shows the slider bar and cables of this device. The speed of the slider bar is equal to the tangent velocity of the pendulum, so that the velocity of the cables is determined by the drop-height of the pendulum and the angle between the cables and the slider bar. The speed of the shuttles is therefore constrained to be less than the pendulum speed. Practical considerations, such as the available rigging space, will determine the lever length of the pendulum, which will apply constraints on the pendulum drop-height.

The pendulum tangent speed is equal to the slider bar speed, which is found by equation 1:

$$v=(2gh)^{1/2}$$

where g is the acceleration due to gravity (9.81 m/s$^2$) and h is the drop-height. Using the maximum drop-height of 1.52 m, as given, the maximum pendulum speed is 5.46 m/s. From FIG. 1, the cable speed is found from the component of the slider bar speed in the cable direction, as equation 2:

$$v_C=v\cos\alpha$$

where $\alpha$ is the angle between the cable and the slider bar. Since the displacement of the shuttles is equal and opposite, the total sample stretching velocity is twice that of the cable velocity. Given that $\cos\alpha \leq 1$, the maximum available sample stretching speed is 10.92 m/s. This maximum speed was incorrectly cited in the references as 16.93 m/s.

There is a need for a tensile impact instrument that provides uniform, homogeneous uniaxial deformation at an essentially fixed strain rate to high strains, with the entire experiment captured on video.

BRIEF SUMMARY OF THE INVENTION

A high-speed tensile test machine configured with a weight on a vertical track, with two L-levers positioned below and on each side of the weight. When the weight is dropped, it pushes the horizontal arms of the L-levers. The L-levers pivot at a point located on the horizontal arm. Two cables are connected to essentially vertical arms of the L-levers and looped around pulleys, then connected to shuttles located on a horizontal track. The shuttles are attached to load cells. The load cells are connected to a grip that holds a sample to be tested. When the weight is dropped, it moves down the vertical track and impacts the horizontal arms of the L-levers, which pivot, causing the cables to pull on said shuttles, load cell, and grip, which move in an outward direction, stretching the sample. The stress-strain behavior of the sample can be measured by any known means, including, but not limited to, a high-speed digital camera. The device measures the stress-strain behavior, up to failure, of polymeric materials, at high strains (as much as 1000%), and high strain rates (up to 10$^4$/s). The high failure strains make the device suited for testing elastomers, which have high elongations to failure. The achievable strain rates are 4 to 5 orders of magnitude greater than that available with current testing machines.

DETAILED DESCRIPTION OF THE INVENTION

A high-speed tensile test instrument is described, capable of measuring the mechanical response of elastomers at strain rates ranging from values much less than unity to at least 2000 s$^{-1}$ for strains through failure. The device employs a drop weight that engages levers to stretch a sample on a horizontal track. To improve dynamic equilibrium, a common problem in high speed testing, equal and opposite loading was applied to each end of the sample. Demonstrative results are reported for two elastomers at strain rates to 588 s$^{-1}$ with maximum strains of 4.3. At the higher strain rates, there is a substantial inertial contribution to the measured force, an effect unaccounted for in prior devices using the drop weight technique.

The strain rates were essentially constant over most of the strain range and fill a three-decade gap in the data from existing methods.

Figure 3:
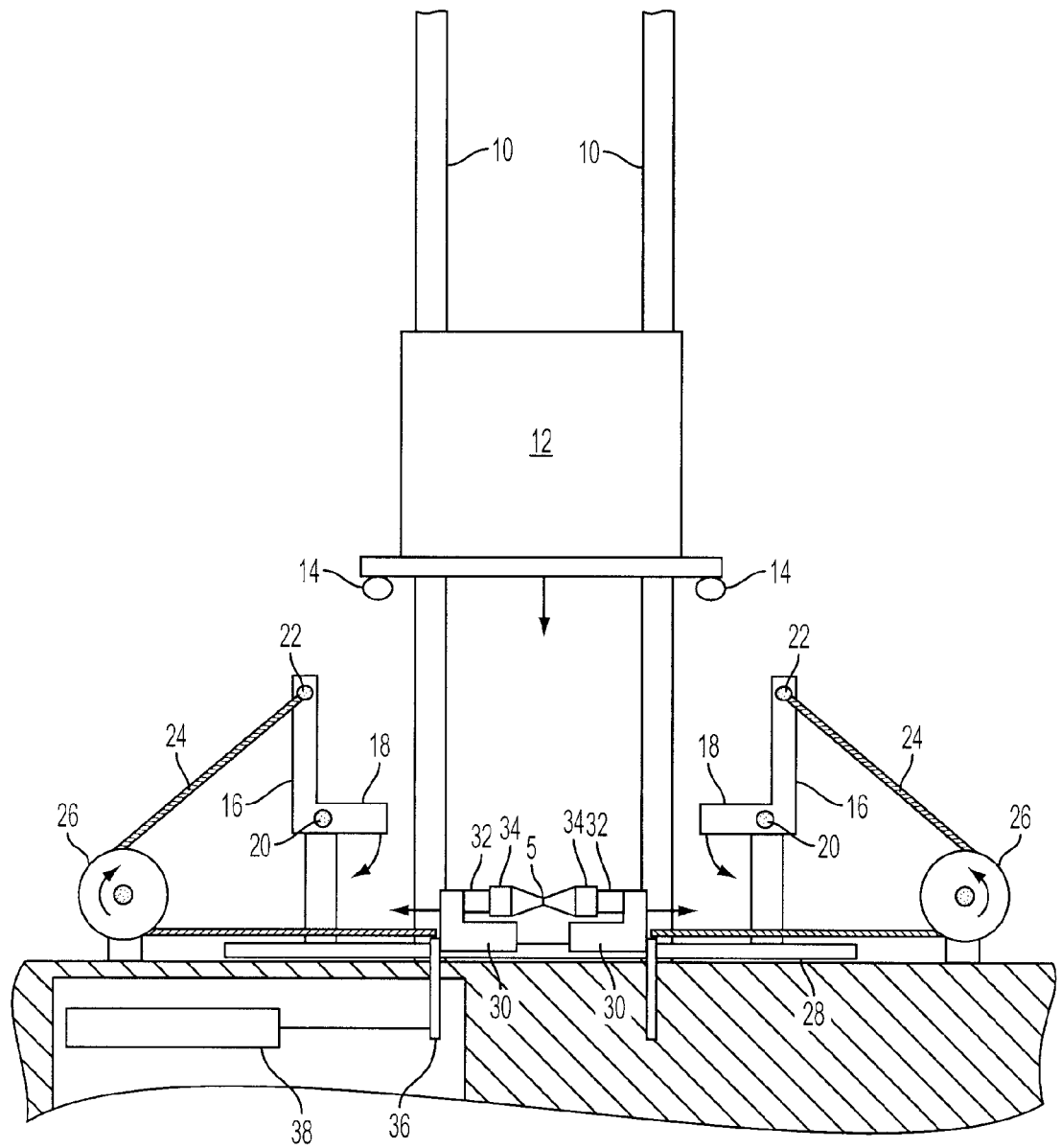
FIG. 3 is a schematic of the present high-speed tensile test instrument.

A schematic of the device is shown in FIG. 3. The weight 12 is raised in a vertical track 10 to a particular height and then dropped. The weight 12 must be large enough to provide the energy to drive the mechanism, and to deform the sample 5 to the required strain; thus, the weight 12 can be relatively low for soft materials. The dropping height is determined by the stretch speed desired. Optionally, attached to the bottom of the weight 12 are two round bars 14 that extend forward from the weight. The bars 14 contact two L-levers 16, although other method of impacting and engaging the L-lever would be understood by those skilled in the art. The weight 12 could contact the L-levers 16 directly as well. The bars 14 contact the horizontal arm 18 of the L-levers 16, pushing the L-levers 16 downward, which causes the L-levers 16 to pivot about a pivot point 20, as the weight 12 passes the L-levers when it falls. Attached near the top of the vertical arm 22 of the L-levers 16 are cables 24, which are pulled inwardly, toward the centerline of the device by the L-levers. The L-levers 16 convert the motion of the falling weight 12 to motion of the cables 24, with the speed multiplied by the ratio of the lever arm lengths. The cables 24 are directed around pulleys 26, and are attached to shuttles 30, which move outwardly, away from the centerline of the device on a horizontal track 28. Thus the pulleys 26 convert the vertical direction of the falling weight 12 to horizontal motion of the shuttles 30. The opposing tensile forces applied through the cables 24 are directed through, and measured by, the load cells 32. Two load cells 32 are used to insure accuracy, although those skilled in the art would understand that adequate results can be obtained with only one load cell. This load is applied to the sample 5. The sample may be any shape used for mechanical testing. The sample 5 is clamped by means of grips 34, which are attached to the load cells 32. The displacement of one of the shuttles 30 is measured by a measuring device. FIG. 3 shows an arm 36 attached to a shuttle 30, which communicates to the displacement measuring device 38. The displacement can be estimated from the motion of the level arms, but for more accurate strain measurement the displacement is determined from video recording of the motion of fiducial marks on the sample.

The displacement measuring device 38 can be a linear variable differential transformer (LVDT), although other devices or means of measuring displacement may be used, such as a high speed video recording device. The latter provides the greatest accuracy of strain measurement. The sample 5 is stretched by the motion of the shuttles 30. The symmetry of the device insures that the displacement of the shuttles 30 is equal and opposite, and therefore the total stretching of the sample is twice the displacement of one of the shuttles.

In addition to measuring the shuttle displacement, the shuttle acceleration also must be measured. This may be accomplished by twice differentiating the displacement revealed by the displacement measuring device 38, or by attaching an accelerometer (not shown) to the shuttles 30. The acceleration must be measured to determine the inertial forces that are included in the force determined by the load cell(s) 32, but are not transmitted to the sample 5 causing it to stretch.

The signals provided by the load cell(s) 32 and displacement measuring device 38 are supplied to a computer with the appropriate conditioning. At maximum sample stretch rate, a typical measurement will require less than 1 ms. Reasonable resolution of the measured load-displacement curve will entail approximately 100 load and displacement data. The required data acquisition rate is therefore 400,000 points per second, although more points are desirable. The vertical track 10, free-falling weight 12, and the L-levers 16 of the present device provide a significant enhancement over the earlier device. These new components increase substantially the range of the displacement rate, as well as the maximum displacement, which can be applied to the sample. The arrangement of components also enhances the uniformity of the strain rate during the test.

Figure 1:
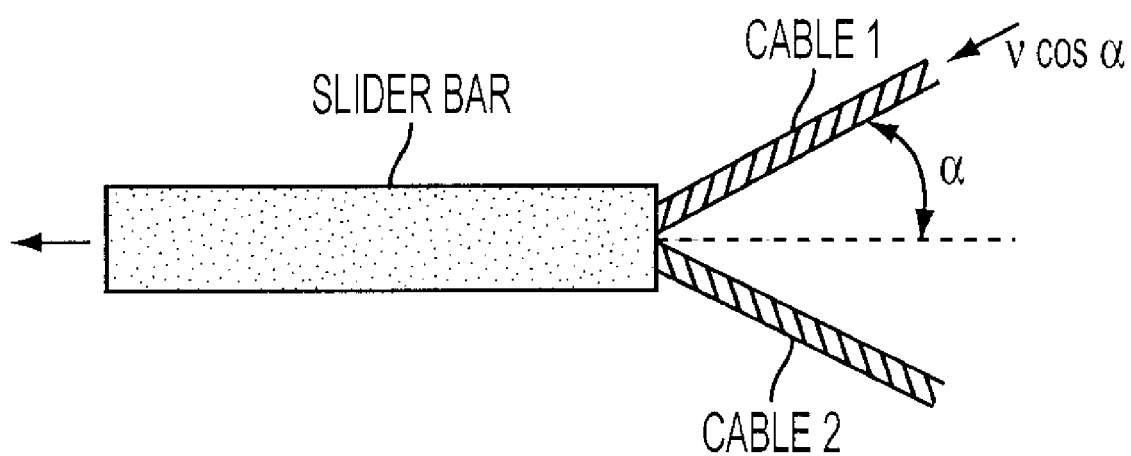
FIG. 1 shows the slider bar and cables of the Hoo Fatt high speed tensile test machine.
Figure 2:
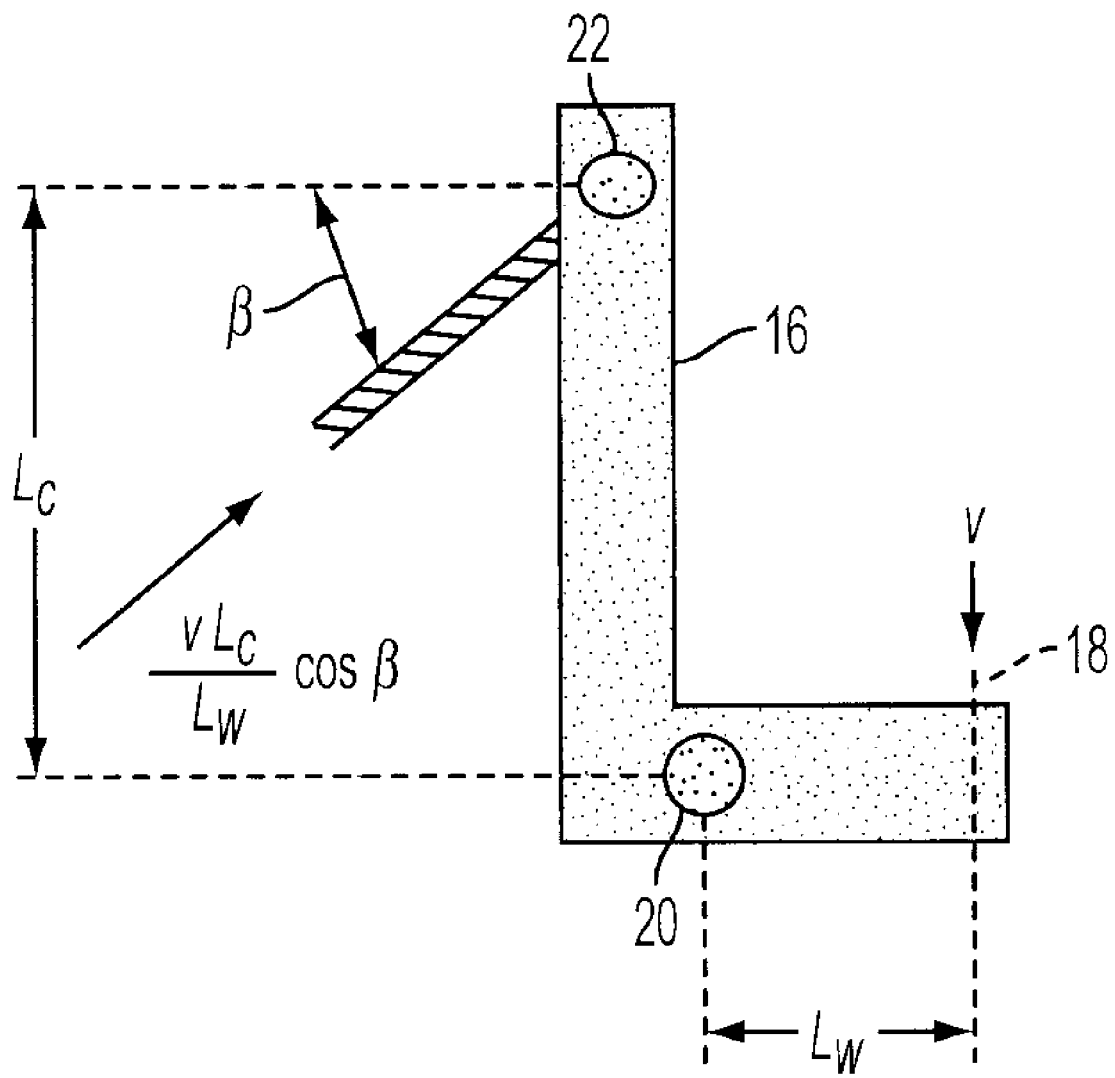
FIG. 2 shows the geometry of L-lever in detail.

For example, if the maximum drop-height in the device is 4.57 m, the maximum speed would be 9.47 m/s. In FIG. 3, the weight 12 impacts the L-levers 16. The geometry of L-lever 16 is shown in detail in FIG. 2. The distance of the weight impact point on the horizontal arm 18 from the pivot point 20 is LW and distance from the pivot point 20 to the cable attachment point 22 is LC, and the cable forms an angle $\beta$ with the tangent velocity of the L-lever 16 at the attachment point 22. The cable speed is determined by Equation 3:

$$v_C = vL \cos \beta$$

where v is the speed of the weight and L is the ratio $L_C/L_W$. The position of the cable attachment point determines the final sample stretching speed (=twice the cable speed), which can be adjusted as needed. The value of L is limited only by practical considerations of the available space to house the instrument. For L=20 (a representative value) the maximum sample stretching speed would be about 379 m/s. This is nearly 35 times greater than that of the earlier devices.

To enable stress-strain curves to be measured at slower strain rates, using the same apparatus, the usefulness of the L-levers becomes apparent; i.e., values of L<1. The minimum weight drop-height is approximately 0.01 m, which provides a weight speed of 0.44 m/s. By using appropriate L-levers and by disconnecting one of the cables and fixing the unattached shuttle, the stretch speed can be decreased by a factor of 20 to 0.02 m/s, which is in the range of speeds of conventional screw-driven test machines.

Figure 4:
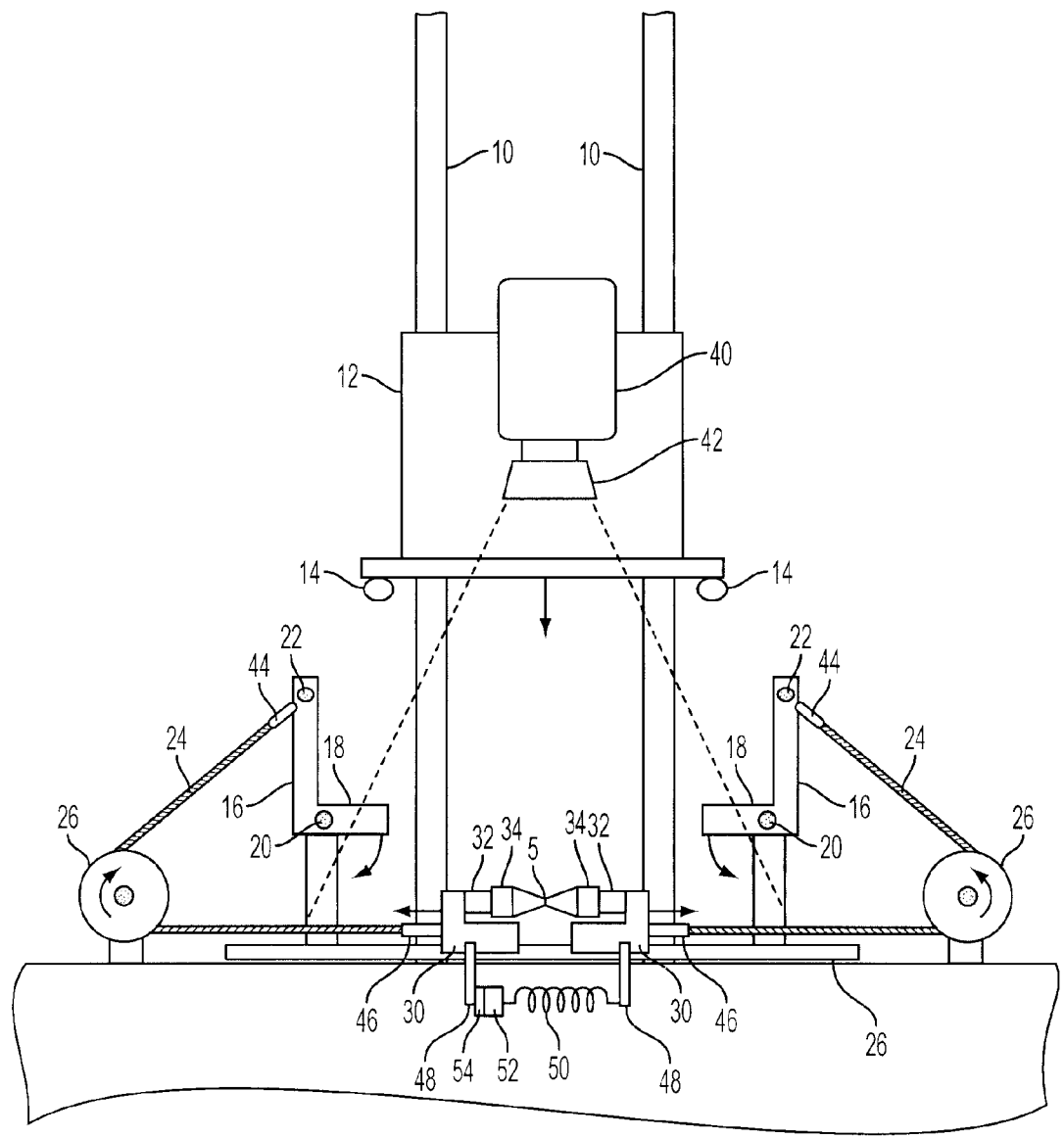
FIG. 4 shows a schematic of the present high-speed tensile test instrument.

FIG. 4 is a schematic of another embodiment of the high-speed tensile test machine. Instead of measuring the displacement of one of the shuttles by an attached arm which communicates to the displacement measuring device, a high speed digital camera 40, such as the Vision Research Phantom 7 monochrome, records the motion, with the positions of fiducial marks, on both the shuttles 30 and the sample 5, determined by image analysis, such as Image Express Motion Plus. The monochrome images with pixel dimensions of 704×96 are recorded in 12-bit resolution. The dimension of the images may be adjusted as desired, to accommodate different sample dimensions and different final strains. The image size may also be adjusted using the zoom lens 42, again to accommodate different sample dimensions and different final strains.

In the second embodiment shown in FIG. 4, optional turnbuckles 44 were included between the L-levers 16 and the cables 24. The turnbuckles 44 provide a final adjustment of the length of the cables 24 to insure that the force acting on the sample is zero at the beginning of the measurement. Optionally, shock absorbers 46 were fitted in the loading train near the shuttles 30 to damp out vibrations occurring during the first 2-3 ms. These were fabricated from 50 mm long nylon reinforced PVC tubing mounted between barbed brass fittings. During the impact, the tubing stretched markedly, damping out high frequency spikes in the measured load. If the shock absorbers are omitted, the force and accelerometer data become much noisier. Optionally, the cables 24 are kept taut by a tension spring 50, which was attached to the shuttles with the brackets 48. At one end of the tension spring 50 is a magnet 52 and magnet striker plate 54. As the tensile force is applied to the cables 24, the tension between the magnet 52 and the magnet striker plate 54 exceeds the holding capacity of the magnet, and the magnet releases, unhindering the shuttles 30. Thus, all of the tensile force in the cables 24 is applied to moving the shuttles 30 and stretching the sample 5.

Having described the invention, the following example is given to illustrate specific applications of the invention, including the best mode now known to perform the invention. These specific examples are not intended to limit the scope of the invention described in this application.

The following illustrates the device performance, using rubber samples stretched at a high strain rate. Two types of rubbers were tested, a nitrile rubber (see Choi et al., Rubber Chem. Technol. 67, 892 (1994)) and a commercial polyurea (Dow Chemical Isonate 143L and Air Products Versalink P1000, 1:4 stoichiometry). Both are high modulus elastomers with substantial toughness. The nitrile rubber was mixed in a two roll laboratory mill and then compression molded into sheets, first at 125° C. for 30 min, and then at 160° C. for 35 min. The polyurea was degassed with an internal mixer, and then sprayed into sheets for curing at room temperature. Test samples from both materials were die cut from the molded sheets.

Two different load cells were employed. For slow measurements, a conventional strain-gauge type load cell such as the Futek LCM300 load cell was used. For fast measurements a piezoelectric load cell, such as the PCB Piezotronics, Inc., Link ICP quartz force sensor was used. The latter self-discharges too quickly for low strain rate experiments, having a half-life of about 9.4 s. Accelerometers, such as PCB Piezotronics, Inc., quartz shear ICP accelerometer, were also attached to the shuttles. Load cell calibration was carried out at low speed, using the winch motor, with a steel spring mounted between the load cells. The force-deflection results were compared to data from measurements with an Instron 5500R. The load cell and accelerometer signals were recorded simultaneously at $10^4$ Hz with an analog-to-digital (A/D) system external to the data computer, such as National Instruments, Inc., high-speed data acquisition system. A signal from a photoelectric sensor, such as Automatic Timing & Controls 7703A, simultaneously triggered the A/D system and the digital camera, which are operated at the same rate of 104 frames/s to simplify data analysis. Timing between the two devices was established by comparing the inertial peak force to the maximum acceleration of the shuttle; it was found that the A/D system inserted a 0.3 ms delay to the data. A comparison of the force and frame index at sample failure, which typically occurs about 30 ms after the trigger, verified that the A/D and digital camera acquisition rates were equal within the precision of the measurement.

Figure 5:
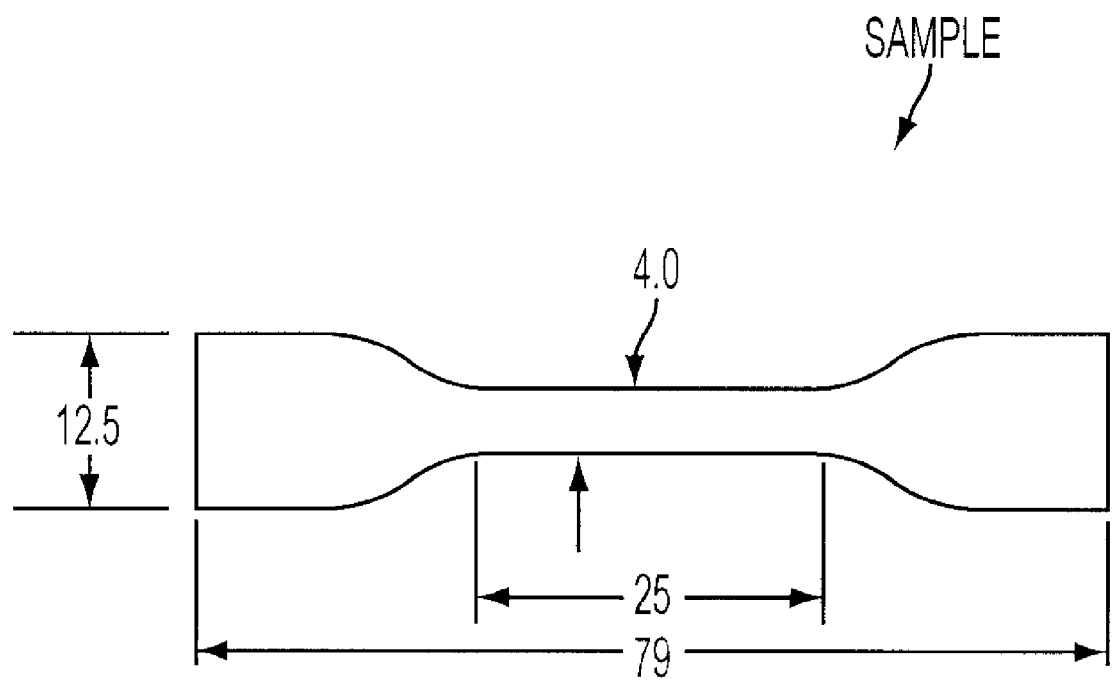
FIG. 5 shows a dumbbell-shaped sample.

The dimensions of the dumbbell-shaped sample, which is conforming to ASTM D4482, "Rubber property-extension cycling fatigue", ASTM International, West Conshohocken, Pa., are given in mm in FIG. 5; the thickness of the sample is approximately 1.5 mm. The strains are determined by the change in length between marks at either end of the 25 mm test section; thus, end effects are avoided.

Figure 6:
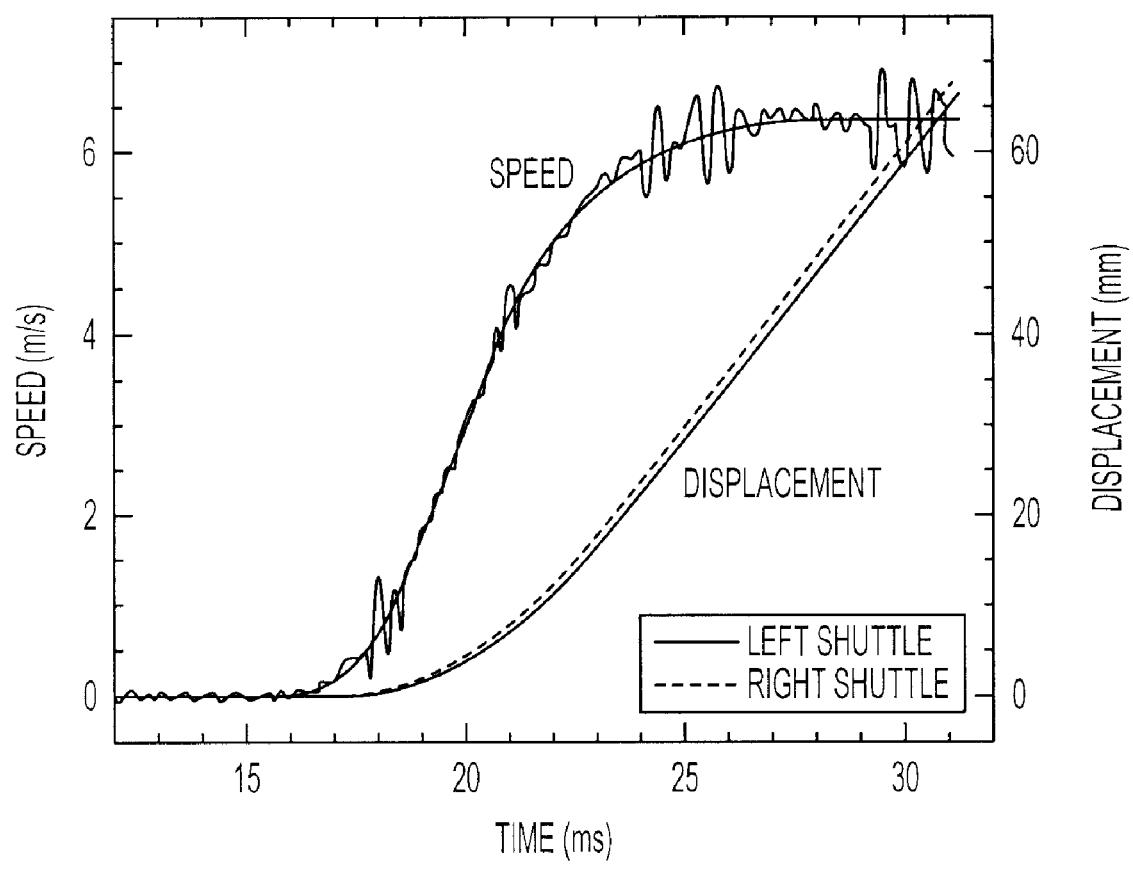
FIG. 6 shows the typical motion of the empty shuttles.

Inertia Correction: Typical motion of the empty shuttles is shown from a 0.229 m drop height without a sample present in FIG. 6. For equilibrium (zero net acceleration of the sample), it is necessary that the forces applied at both ends of the sample remain equal throughout the measurement. This is accomplished by attention to symmetry: the L levers must be the same distance from the impact bars (adjusted using shims), at the same angle to the vertical (adjusted using stops), and centered between the impact bars (adjusted by moving the base). The displacement was fit to the Gompertz growth curve (Equation 4) (see Gompertz, Philos. Trans. R. Soc. London 123, 513 (1825))

$$s = s_M \exp\{-\exp[-k(t-t_0)]\} \quad \text{Equation 4}$$

where $s_M$ is the maximum speed, $t_0$ is the offset time, and k is the sharpness of the S-shaped inflection. This expression was chosen for its simplicity and fidelity to the data. FIG. 6 shows that the difference between the start of the shuttle movements, as determined by fitting the sample speed to Eq. 4, was less than 1 ms, with the shuttle speeds differing by no more than 0.2 m/s at the conclusion of the test. This is a typical result and experiments that exceeded these differences are discarded. Shuttle speeds herein ranged from about 4 to about 10 m/s, depending on the drop height. Using the maximum available height, shuttle speeds of about 26 m/s can be achieved.

FIG. 6 also shows the shuttle speed s as determined by numerical derivative of the displacement. The left shuttle speed was found by numerical differentiation; the right shuttle speed was indistinguishable from the left and has been omitted for clarity. The smooth line in FIG. 6 is the fit to the shuttle speed from Eq. 4, with $s_M=6.41$ m/s, $t_0=9.26$ ms, and $k=538.8$ s$^{-1}$.

In conventional stress-strain test measurements, the highest displacement rate does not exceed about 0.01 m/s, with corresponding strain rates of about 0.1 s$^{-1}$. Inertial forces in such measurements can be neglected since they are smaller than other sources of error, for example load cell drift due to temperature fluctuations. In the high rate measurements discussed herein, however, the inertial force can be substantial, so it must be subtracted from the total force. The shuttle acceleration a was then found from the derivative (Equation 5)

$$a = s_M k \exp\{-k(t-t_0) - \exp[-k(t-t_0)]\}$$

Figure 7:
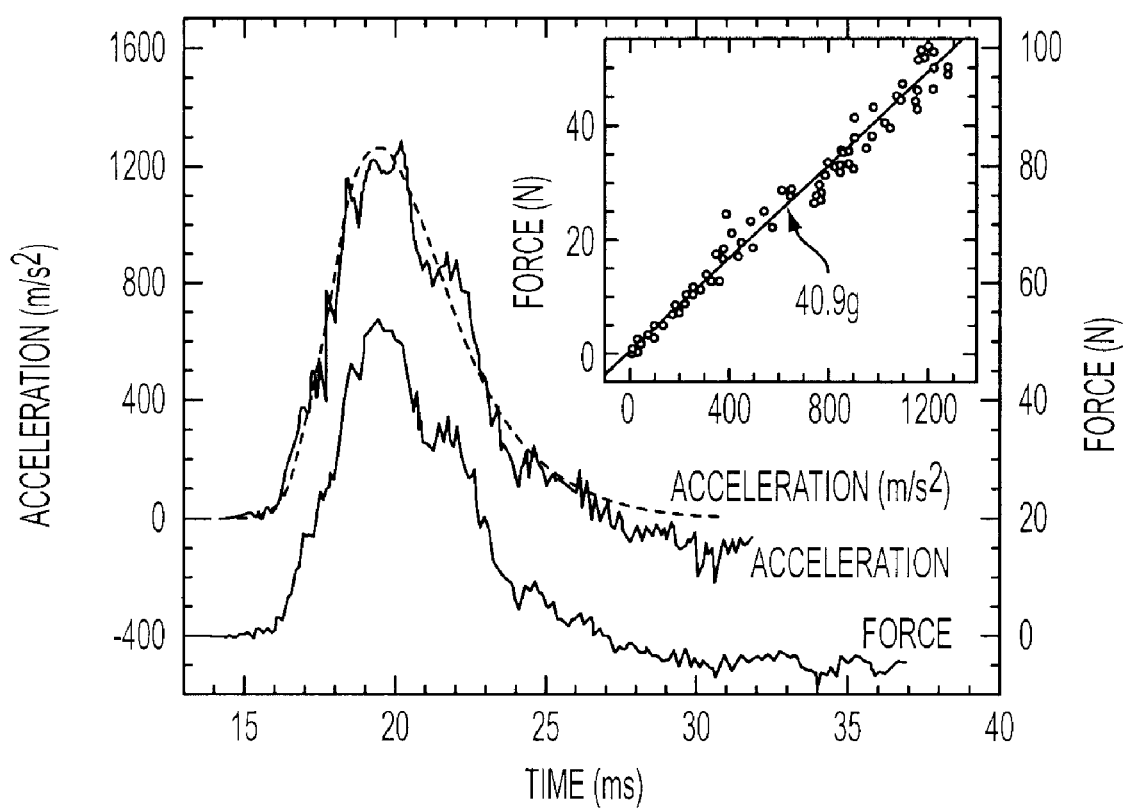
FIG. 7 shows the force from the piezoelectric load cell, the output of the accelerometer, and the acceleration determined from the derivative of the shuttle speed, all plotted as a function of time.

FIG. 7 shows the force from the piezoelectric load cell, the output of the accelerometer, and the acceleration determined from the derivative of the shuttle speed, all plotted as a function of time. The agreement between these data and the fit of Eq. 5 is excellent, verifying the accelerometer calibration.

Figure 8:
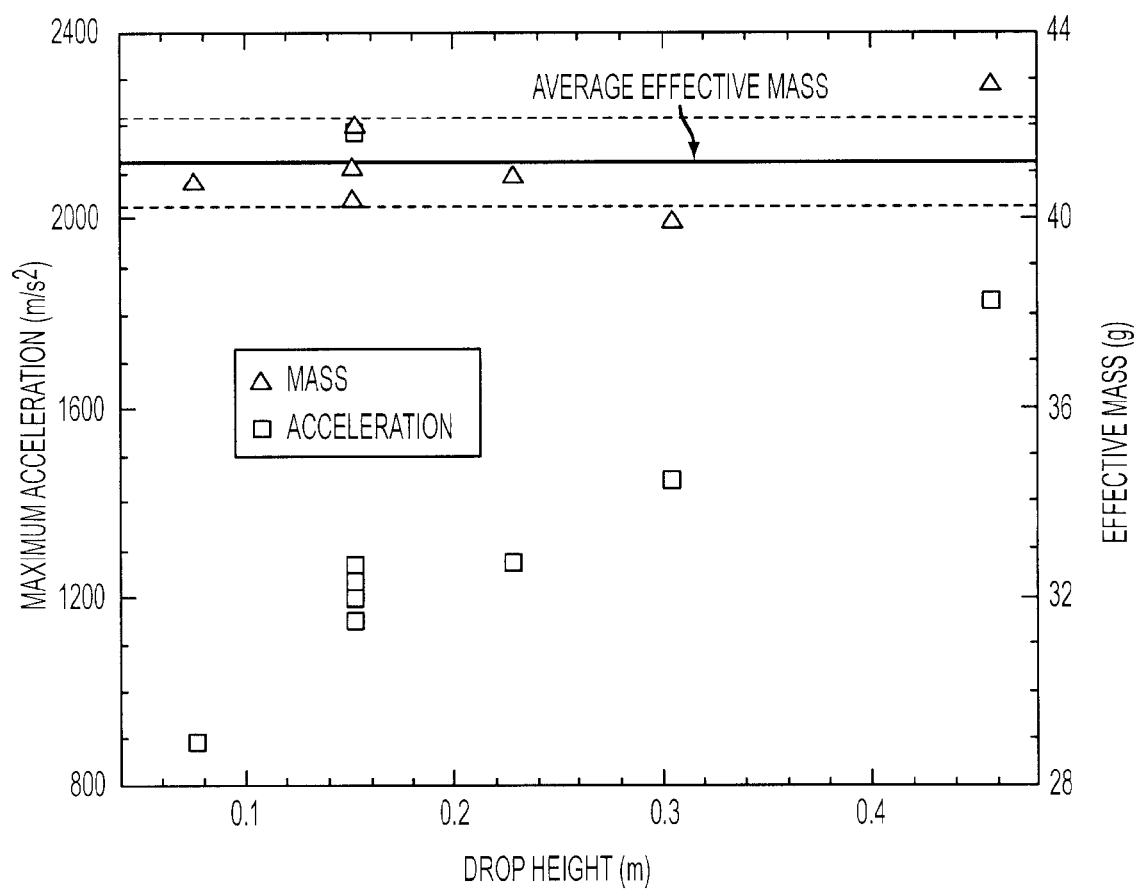
FIG. 8 shows effective mass along with the maximum acceleration displayed as a function of drop height.

The force F in FIG. 7 is the result of the acceleration a of the grips and other hardware attached to the sensing end of the load cell. The two quantities are related by Equation 6:

$$F = ma,$$

where m is the effective mass of the grip hardware. Comparing the positions of the small fluctuations in the accelerometer and force data, it is clear that these features reflect genuine changes in the movement of the shuttles, not artifacts due to noise. It is also evident that the accelerometer is more faithful to the shuttle acceleration than the fit to the image analysis data. At times beyond 27 ms, both the force and the accelerometer are slightly negative, indicating that the shuttle is slowing. This behavior is difficult to discern, given the scatter in the shuttle speed data in FIG. 6, nor is it captured by the fit using Eq. 4. The inset in FIG. 7 shows the measured force as a function of the accelerometer response; these data are linear, passing through the origin with a slope equal to the effective mass. This mass, along with the maximum acceleration (from Eq. 5), are displayed as a function of drop height in FIG. 8. The maximum acceleration varies from 893 to 1826 m/s$^2$, with the effective mass found to be constant, equal to 41.2±0.9 g (the error is one standard deviation). This mass reflects the weight of the grip, stud, and two jam nuts, plus the intrinsic (internal) inertia of the piezoelectric load cell. Similar measurements carried out after removal of the detachable hardware yielded an effective mass of 18.94±1.2 g. The difference, 22.3 g, compares well with the actual weight of the grip hardware, 20.24 g. For comparison, the sample weight was typically about 1.5 g. A similar set of measurements was carried out for the other shuttle, fitted with the conventional load cell. The effective mass was 11.8 g, which was reduced by 9.6 g with all hardware removed. This compares well to the actual weight of the hardware, 9.4 g. The lower mass of this shuttle is due to differences in configuration.

Figure 9A:
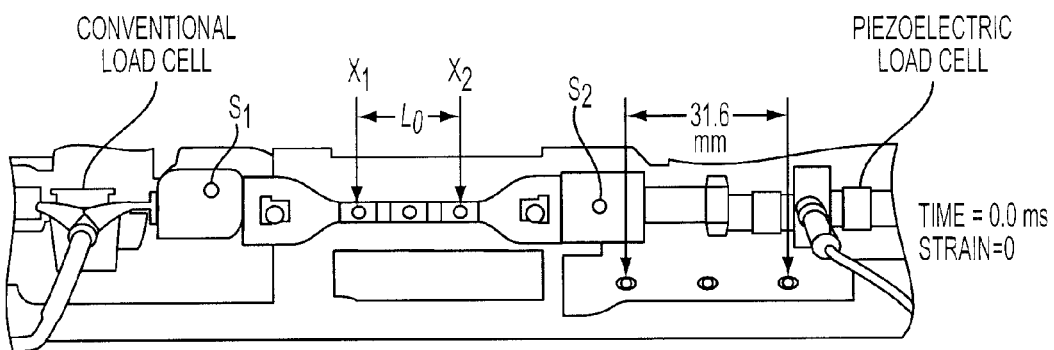
FIGS. 9a-9d show a sequence of four figures of a test of the nitrile rubber.
Figure 9B:
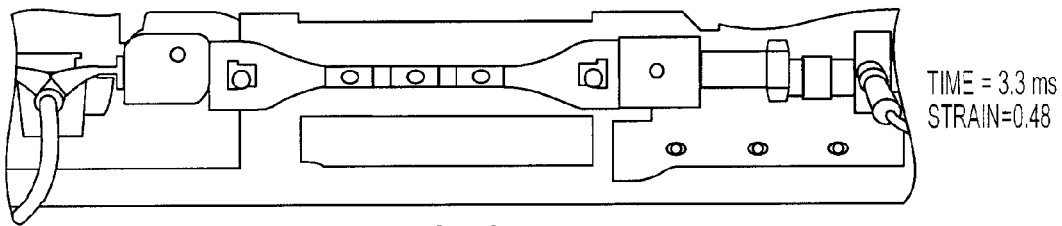
Figure 9C:
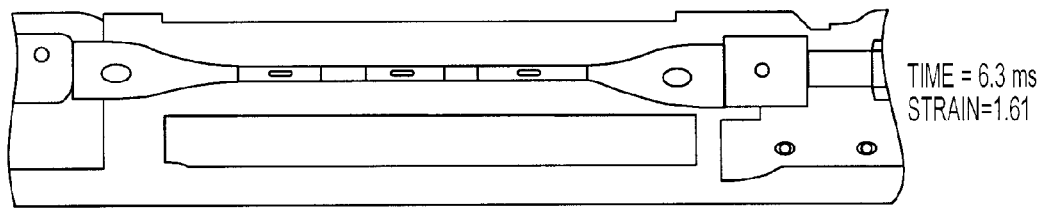
Figure 9D:
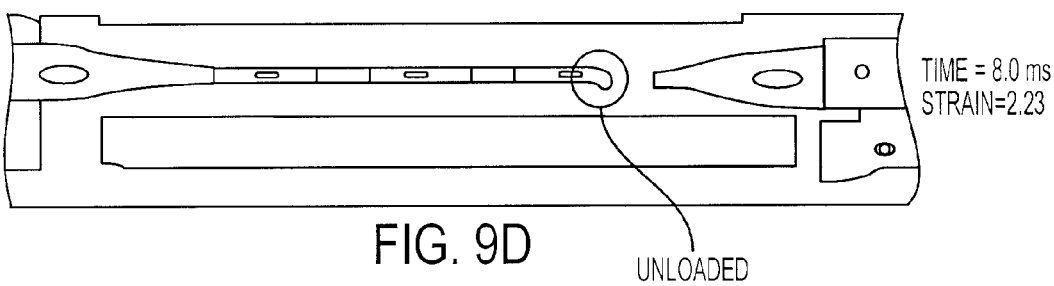

Strain: FIGS. 9a-9d show a sequence of four figures of a test of the nitrile rubber. The marks $x_1$ and $x_2$ identify the ends of the uniform sample gauge length and $S_1$ and $S_2$ identify the grip positions. The images at 3.3 ms (FIG. 9b) and 6.3 ms (FIG. 9c) show that the gauge length region is deforming uniformly, without propagating waves. Interestingly, at 6.3 ms the gauge length has changed to a "white" color in the black and white image. In other stress-strain measurements, carried out at a strain rate of 0.1 s, the rubber also turned white at large strain; the cause is unknown. FIG. 9d shows the failure of the specimen at 8.0 ms shows a small portion to be unloaded. Since the failure occurred in the uniformly strained test region, the failure strain and stress can be determined.

Figure 10:
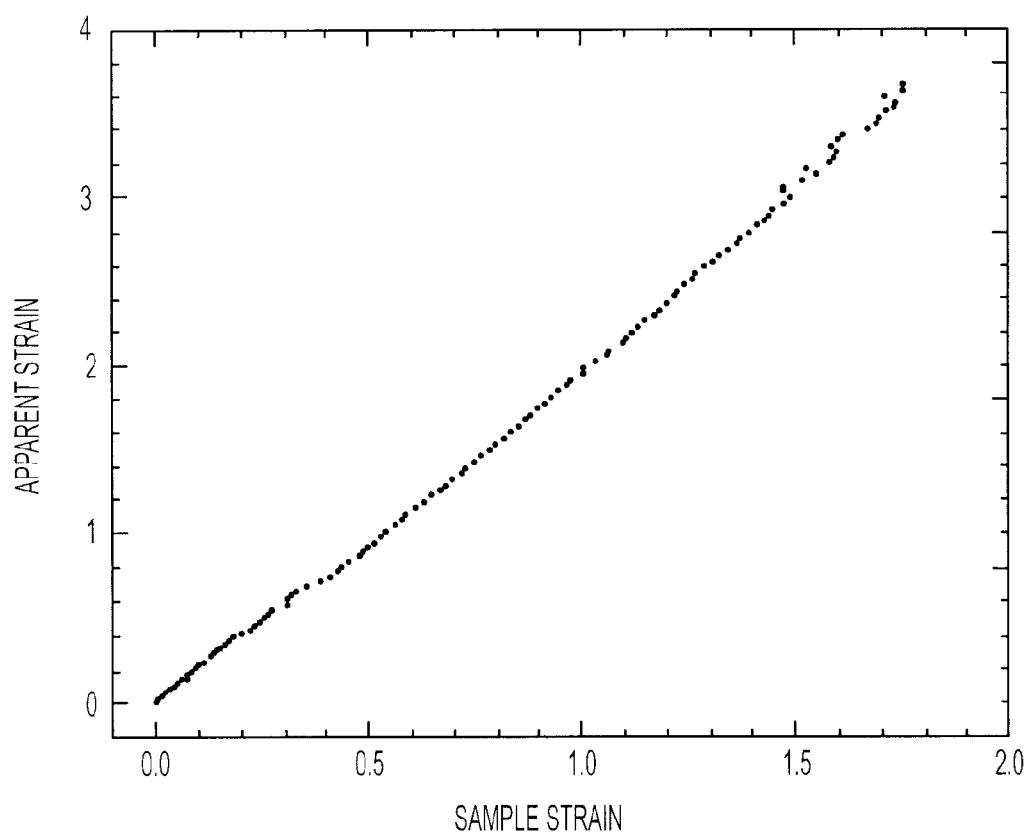
FIG. 10 shows the comparison of apparent strain, found by the relative displacement of points $S_1$ and $S_2$ in FIG. 8, to the actual strain, found by the relative displacement of points $x_1$ and $x_2$.
Figure 11:
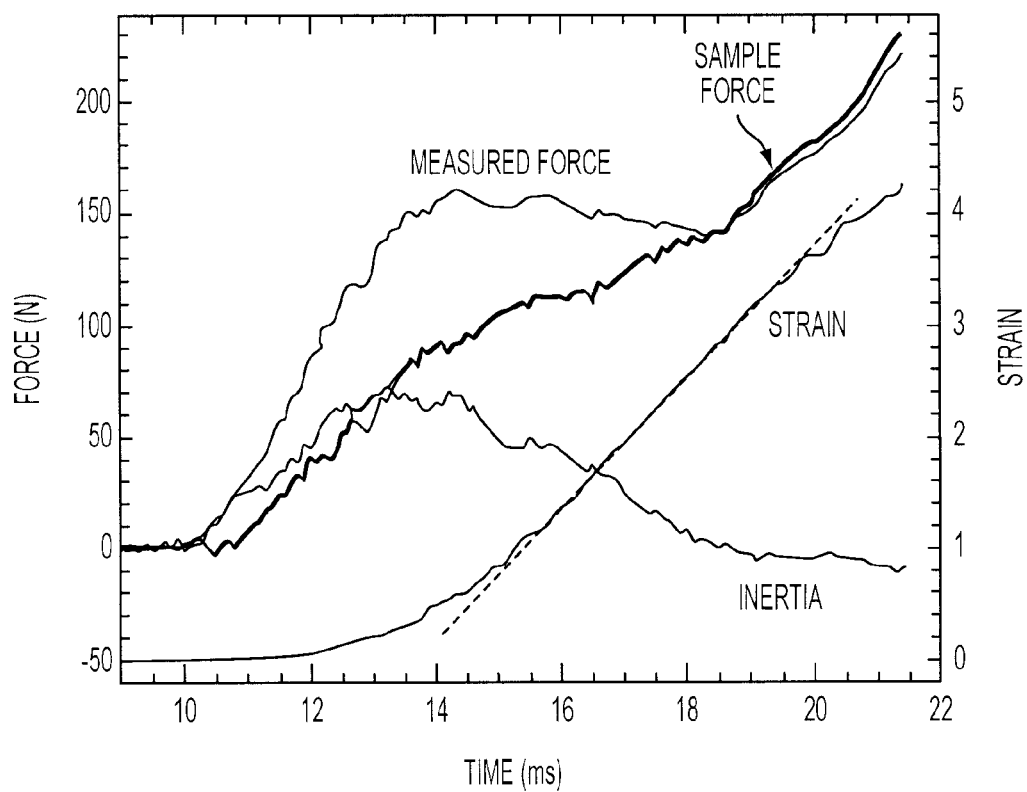
FIG. 11 shows forces from the piezoelectric load cell, deduced from the accelerometer (inertia) and calculated for the polyurea sample with a 0.61 m drop height.

FIG. 10 shows the comparison of apparent strain, found by the relative displacement of points $S_1$ and $S_2$ in FIG. 9, to the actual strain, found by the relative displacement of points $x_1$ and $x_2$. FIG. 11 shows forces from the piezoelectric load cell, deduced from the accelerometer (inertia) and calculated for the polyurea sample with a 0.61 m drop height. The strain was obtained from the camera images. Note the offset between the strain and the load scales. The dashed line shows the range of constant strain rate; its slope is 588 s$^{-1}$. A comparison of the engineering strain measured in two different ways is shown in FIG. 10. The ordinate is the apparent strain, determined from the displacement of the sample grips $S_1$ and $S_2$ in FIGS. 9a-9d, normalized by the gauge length, $L_0$ in FIGS. 9a-9d. The abscissa represents the actual strain, obtained from the displacement of the points at the end of the gauge length, $x_1$ and $x_2$ in FIGS. 9a-9d, normalized by $L_0$. The apparent strain overestimates the actual strain by a factor of 2. The apparent strain rate would have the same error; thus, strain rates reported from shuttle displacements overestimate the strain rate, by an amount depending on the sample shape. This explains why using photographic images of fiducial marks is more accurate than using an LVDT to measure displacements.

Immediately after the sample fails, at 8.0 ms, in figure of FIG. 9d, the specimen retracts after an unloading wave passes through the length of the sample. See Mason, Proc. R. Soc. London, Ser. A 272, 315 (1963). The unloading wave moves as a pulse at a constant speed $v_u$, determined in separate experiments to be 1001±72 and 320±20 m/s at 100% strain for the nitrile and polyurea compounds, respectively. The unloading wave is isochorically constrained to one dimension, and is different from a longitudinal wave that occurs in three dimensions with volumetric strain. The unloading wave speed is $$v_u = (1+e)(E/\rho)^{1/2}$$

where e is the engineering strain, E is Young's modulus, and $\rho$ is the density. See Gent et al., J. Appl. Phys. 53, 6069 (1982), James et al., Phys. Rev. 66, 33 (1944), and Mrowca, et al., J. Appl. Phys. 16, 8 (1945). The one-dimensional unloading wave speed is sensitive to the strain, and is approximately $\frac{1}{50}$ of the more familiar longitudinal wave speed. After the unloading wave passes, the unloaded rubber undergoes strain recovery at a slower rate that depends on the viscoelastic response of the polymer. Assuming that a loading pulse is identical to an unloading pulse, the speed of the unloading wave establishes both the maximum strain rate that can be achieved in a dynamically homogeneous measurement and also the time resolution. The maximum strain rate is $$\epsilon_{max} = v_u/L_{tot}$$

where $L_{tot}$ is the total distance the unloading wave must travel (=½ the distance between the grips, or approximately 30 mm). Thus, the maximum strain rate is about 33 000 and 10 700 s$^{-1}$ for the nitrile rubber and polyurea, respectively. These values are 1.5-2 orders of magnitude greater than the strain rates attained herein. The time resolution, or time required for a pulse to travel down the sample, is just the reciprocal the above equation, and equal to 0.03 and 0.09 ms for the nitrile rubber and polyurea, respectively. Data taken over such time intervals, or taken at deflection rates approaching the loading wave speed, reflect a transitory wave and are therefore not kinematical. The tensile behavior of an elastomer tested at speeds greater than the loading wave is predicted to be either a rarefaction wave or a shock, or a combination of the two. See, Knowles, J. Appl. Math. 62, 1153 (2002).

Stress-Strain Curves: The forces measured by the piezoelectric load cell and the inertial forces from accelerometer data are displayed in FIG. 11, for the polyurea using a 0.61 m drop height. The inertial force was found from the product of the acceleration and the separately measured effective inertial mass. The sample force was found by subtracting the inertial force from the measured load. Over the first 0.8 ms, from the start at 10 ms until 10.8 ms, inertia accounts for nearly all of the force, consequently delaying the start of the sample loading. Inertia continues to contribute significantly though 18.7 ms. Afterward, the inertial force is negative due to a small deceleration of the shuttle and from this point onward the sample load slightly exceeds the measured force. FIG. 11 shows that the strain is also delayed from the start by about 0.8 ms. It smoothly accelerates up to a strain of 1.13 at 15.6 ms, whereupon it becomes linear. Beginning at a strain of 3.26 at 1.92 ms, there is slight deceleration. The strain rate in the linear region was 588 s$^{-1}$.

Figure 12:
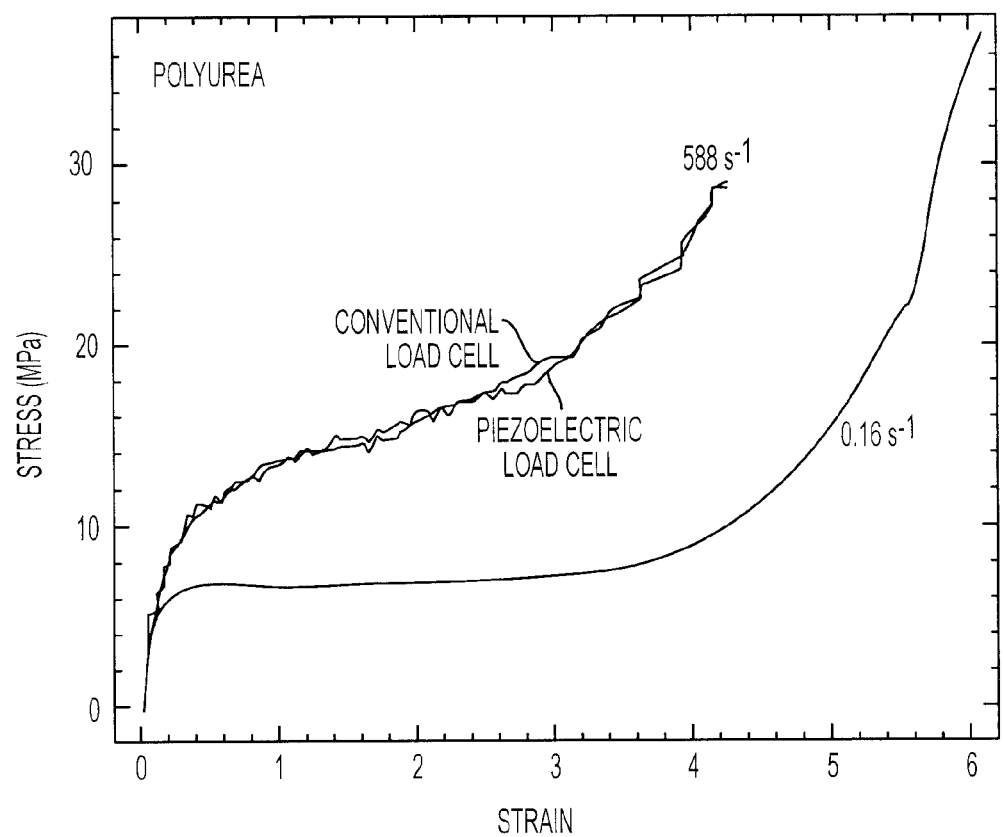
FIG. 12 shows compares the sample forces (inertia corrected) from each load cell, normalized by the original cross-sectional area.

The resulting engineering stress-strain curve from this measurement is shown in FIG. 12. This figure compares the sample forces (inertia corrected) from each load cell, normalized by the original cross-sectional area. The two curves are in agreement within the scatter. The fact that the forces at each end are equal confirms the absence of net acceleration of the sample. For comparison, FIG. 8 also displays the stress-strain behavior measured with an Instron machine at a much lower strain rate. This curve is lower due to greater relaxation of the polyurea during the loading.

Figure 13:
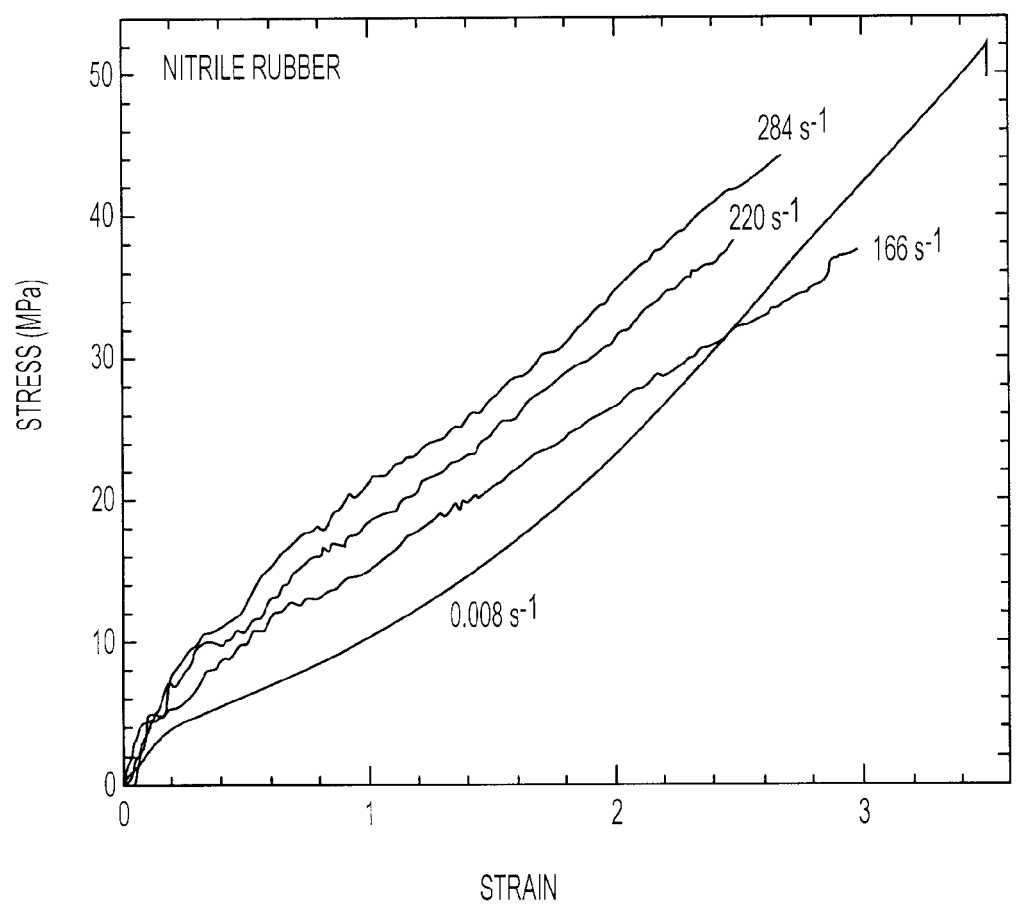
FIG. 13 shows the engineering stress-strain curves for the nitrile rubber at varying strain rates.

Engineering stress-strain curves for the nitrile rubber at varying strain rates are displayed in FIG. 13. The curves for the higher strain rates show the stress increasing with strain rate. Interestingly, the curve for 0.008 s$^{-1}$ crosses the curve for 166 s$^{-1}$, at a strain of 2.45; the reason for this is unknown (the elastomer is a random copolymer and thus not expected to crystallize). One possible difference is nonisothermal conditions for the adiabatic high strain rate test. Comparing FIG. 12 to FIG. 13, the nitrile rubber is much stiffer than the polyurea; consequently, for a given drop height, the strain rate in the nitrile rubber was somewhat lower (and $v_u$ higher).

Having described the invention, the following example is given to illustrate specific applications of the invention, including the best mode now known to perform the invention. These specific examples are not intended to limit the scope of the invention described in this application.

Stress strain measurements were conducted for an elastomeric polyurea in uniaxial tension over a range of strain rates from 0.06 to 573 s$^{-1}$. The experiments were carried out on the second embodiment of the present device, which provides mechanical data at strain rates up to 1000 s$^{-1}$, filling the gap between conventional low speed instruments and split Hopkinson bar tests. The tensile data obtained herein are compared with recent high strain rate compression data on the same material. Advantages of the present measurements include a more uniform strain rate and the ability to ensure homogeneous strain.

The material studied herein is an elastomeric polyurea. Polyureas have been used commercially for more than a decade. Many applications of polyureas involve impact loading, motivating the study of the mechanical response of the material under high strains and high strain rates.

The polyurea was formed by the reaction of a modified diphenylmethane diisocyanate prepolymer (Isonate 143L from Dow Chemical; 144 g/eq) with an oligomeric diamine curative (Versalink P1000 from Air Products; 600 g/eq), in the ratio of 1:4 prepolymer to curative by weight (96% stoichiometry). Test specimens conforming to ASTM D4482 were die cut from cast sheets. For the high-speed testing, strains were determined from the position of fiducial marks, using a digital camera (Vision Research Phantom 7 monochrome). Images (704×96 pixels) were recorded in 12-bit resolution at 10 000 frames/s. The video was analyzed using commercial software (Image Express Motion Plus) to obtain the position of the marks as a function of time during a test. Stresses were measured with two load cells: conventionally by a strain-gauge type (Futek LCM300) and for fast measurements with a piezoelectric load cell (PCB Piezotronics, Inc. Link ICP Quartz Force Sensor), which self-discharges in a few seconds. To measure and correct for inertia, accelerometers (PCB Piezotronics, Inc. Quartz Shear ICP Accelerometer) were attached to the shuttles. Additional measurements were made at low strain rate <0.1 s$^{-1}$ using an Instron 5500R with strains determined by an optical extensometer.

For the high rate experiments herein, the shuttle speeds and accelerations are as high as 10 m/s and 2000 m/s$^2$, respectively. At these rates it is necessary to subtract the force to accelerate the grips and other hardware. The inertia was quantified by tests sans specimen, with both forces and shuttle accelerations measured separately. The obtained inertial masses (conventional load cell, 12 g; piezoelectric load cell, 41 g) agreed with the respective weights of the hardware. The inertial forces were found from the product of the inertial mass and the measured acceleration, the latter determined from the accelerometers Correcting for inertia changes the shape of the stress-strain curves significantly, with the two load cells now yielding equivalent results.

Figure 14:
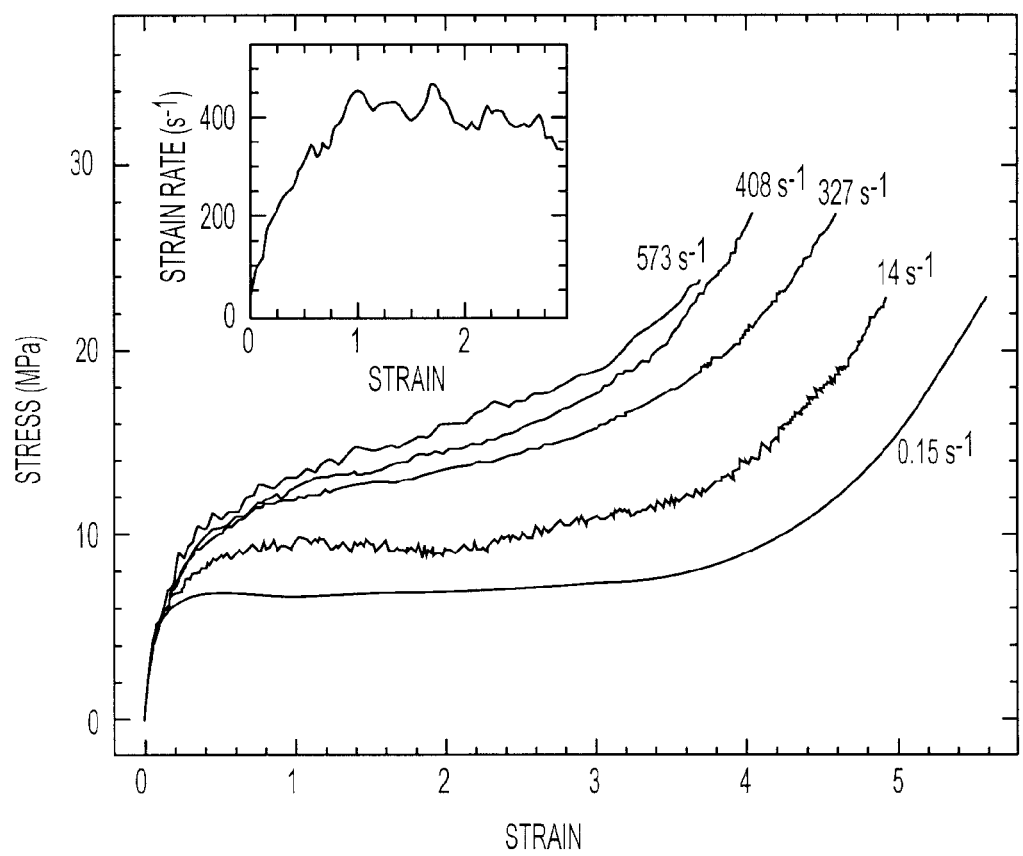
FIG. 14 shows the engineering stress vs. strain measured.

FIG. 14 shows the engineering stress vs. strain measured on an Instron (lowest curve), using a winch to lower the drop weight (second curve from bottom), and for drop heights equal to 0.152, 0.305, and 0.61 m (middle through uppermost curves, respectively, all corrected for inertial forces), with the corresponding engineering strain rates as indicated. The inset shows the typical variation of strain rate over the course of a test. The initial stretching is linear, with a modulus (slope) approaching 100 MPa at the highest rate. Although the yield strains are comparable, the yield stress increases by more than a factor of 2 over this range of rates. As expected from general viscoelastic behavior, the failure stress increases and the failure strain decreases with strain rate, although repeat testing would be required to obtain statistically significant failure properties.

Figure 15:
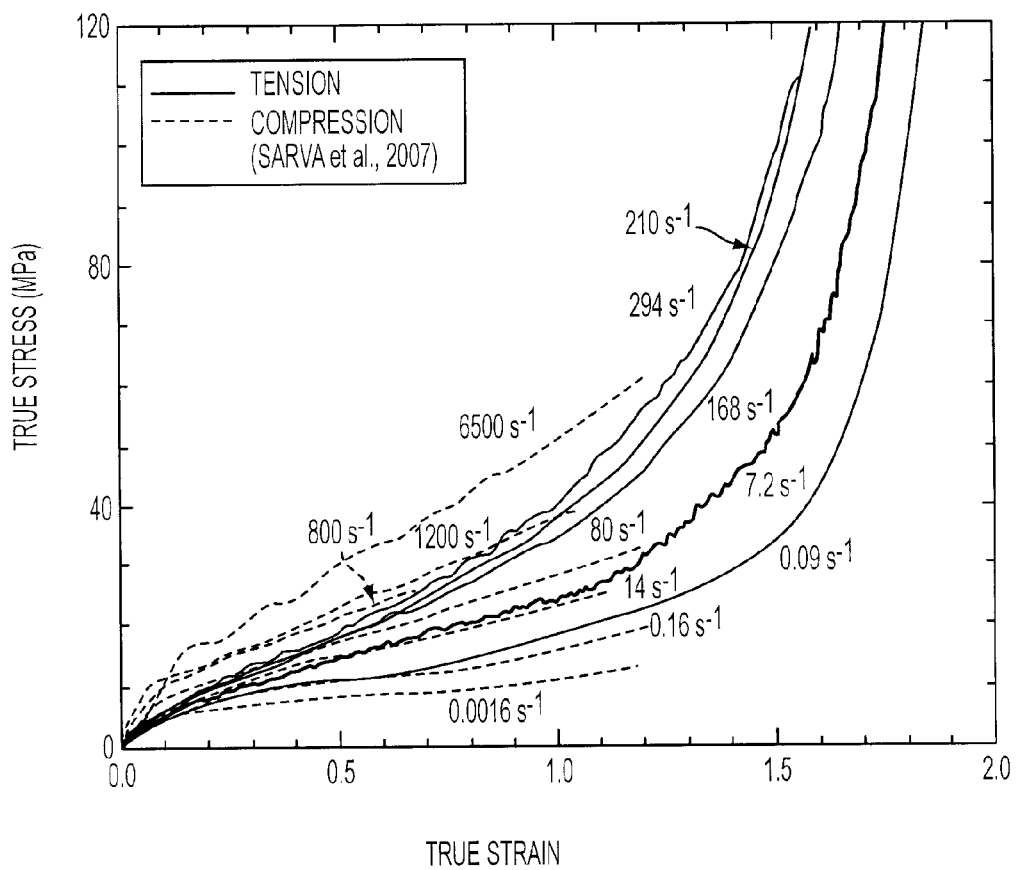
FIG. 15 shows the data from FIG. 14 plotted as the true stress as a function of true strain.

FIG. 15 shows the data in FIG. 14 (solid symbols) plotted as the true (Cauchy) stress $\sigma_T (=\sigma/(\in+1))$ as a function of true (Hencky) strain, $\in_T (=\ln(\in+1))$, along with split Hopkinson bar compression results and one slow strain rate curve from Yi et al., Polymer 47, 319 (2006) (hollow symbols). The split Hopkinson bar strain rates are averages. All of the data in FIG. 15 are of the same polyurea, taken from a single cast sheet. Near the origin ($\in$<½) the tension data have a lower slope, consistent with the behavior expected for elastic equilibrium—the modulus is a decreasing function of tensile strain due to mitigation of the entanglement constraints. However, in compression this effect is weaker or absent. Another noticeable difference between the tension and compression data in FIG. 15 is the apparent effect of strain rate. While for tension there is an expected continuous increase in stiffness with increasing rate, the compression data become essentially invariant to rate at the high strain rates.

Figure 16:
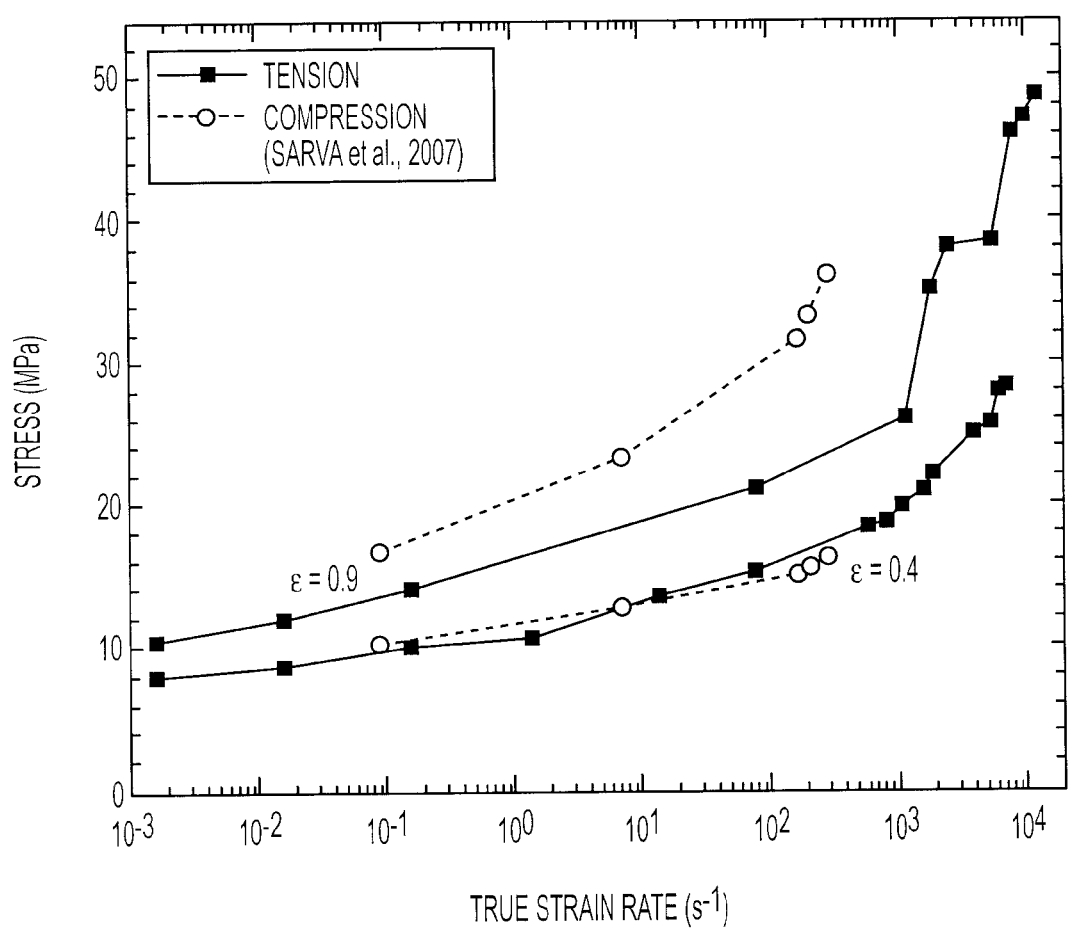
FIG. 16 shows the true stress for $\in=0.3$ is plotted vs. the (engineering) strain rate.

In FIG. 16 the true stress for $\in$=0.3 is plotted vs. the (engineering) strain rate, with the inclusion of low rate (Instron) compression results. The modulus in compression varies monotonically with rate for low strain rates, with a marked change on going from 1 to 1000 s$^{-1}$; the change in the rate dependence over this range is much larger than for tension. These results, however, must be interpreted with some caution, given the sensitivity of the mechanical properties to stoichiometry. Also it should be noted that the strain rate in an split Hopkinson bar measurements increases with strain, so that the values for compression in FIG. 18 are averages.

There does not appear to be any indication of a transition from rubbery to glassy behavior in the results of FIG. 16, as had been suggested by Yi et al. Dielectric relaxation measurements on this material indicate a broad glass transition zone centered at 10$^6$ Hz at room temperature.

The vertical track, the free-falling weight, and the L-levers of the present device provide a significant enhancement over the earlier devices. These increase both the maximum available shuttle speeds and the maximum displacement of the device. The strain rate is essentially constant over a substantial portion of the stress-strain curve. The use of a dog bone-shaped samples together with high speed imaging enables accurate strain measurement, as well as the determination of the strain and stress at failure. The inclusion of accelerometers on the shuttles permits inertia to be measured and subtracted from the stress/strain curves. The difference between the measured and the sample forces shows the significance of this correction. The minimum and maximum available strain rates for this instrument are governed by practical considerations but those skilled in the art would understand that the strain rates discussed herein may be expanded. The lowest strain rate to date, 14 s$^{-1}$, was achieved using a winch motor to lower the weight. Those skilled in the art would understand that using a sample with a longer test section, anchoring one of the shuttles, and other minor modifications can be employed to decrease this by a factor on the order of 10, which would approach the strain rate of conventional, for example, screw-driven instruments. The highest strain rate reported to date, 588 s$^{-1}$, corresponds to a 0.61 m drop height.

The maximum drop height with the test configuration was 4.57 m. Since the speed of the falling weight is $$s_W = (2gh)^{1/2},$$

where g is the acceleration due to gravity (9.81 m/s$^2$) and h is the drop-height, the maximum strain rate is about 2000 s$^{-1}$. The shock absorbers, used to reduce vibrations at the onset of a test, reduce the actual shuttle speeds. Also, as the speed is increased, the shuttle acceleration occurs over a larger portion of the test, reducing the range of constant strain. These limitations may be overcome to some extent by modifying the geometry of the sample, the shock absorbers, and the L levers.

Different types of load cells may be used. In addition, an accelerometer may be added to the one of the shuttles to provide a more precise determination of the initiation of the impact. High-speed photography may be added, to correlate the measured stress-strain behavior to the failure of the sample.

Obviously, many modifications and variations of the present invention are possible in light of the above teachings. It is therefore to be understood that, within the scope of the appended claims, the invention may be practiced otherwise than as specifically described.

What is claimed as new and desired to be protected by Letters Patent of the United States is:

1. A high-speed tensile test machine comprising:
   a weight located on a vertical track,
   two L-levers, said L-levers having a horizontal arm and an essentially vertical arm, said L-levers positioned below and on each side of said weight so said weight pushes said horizontal arms when said weight is dropped, said L-levers having a pivot point located on said horizontal arm, said L-lever being connected to a base at said pivot point;
   two cables, connected to said essentially vertical arms of said L-levers, said cables being directed around a pulley and connected to shuttles located on a horizontal track;
   at least one load cell in connections with said shuttles, wherein said load cell is connected to a grip configured to hold a sample to be tested; and
   a device configured to measure the stress-strain behavior of said sample, wherein when said weight is dropped on said vertical track, said weight pushes downward on said horizontal arm of said L-levers, which pivot about said pivot point, which causes said cables to pull on said shuttles, which move in an outward direction.

2. The device of claim one further comprising two bars extending outward from the bottom of said weight.

3. The device of claim one further comprising turnbuckles connected to said cables.

4. The device of claim one further comprising shock absorbers near said shuttles.

5. The device of claim one further comprising a tension spring located between the two shuttles.

6. The device of claim one wherein said measuring device is a high speed camera.

7. The device of claim one wherein said measuring device is a linear variable differential transformer.

8. The device of claim one further comprising an accelerometer attached to said shuttles.

* * * * *